(12) United States Patent
Johnson et al.

(10) Patent No.: US 7,833,289 B1
(45) Date of Patent: Nov. 16, 2010

(54) HAIR CARE COMPONENT AND METHOD OF MANUFACTURE FOR USE IN A HAIR COLORING SYSTEM

(75) Inventors: Paul Johnson, Beverly Hills, CA (US); John Garruto, Oceanside, CA (US)

(73) Assignee: Alterna Holdings Corporation, Los Angeles, CA (US)

( * ) Notice: Subject to any disclaimer, the term of this patent is extended or adjusted under 35 U.S.C. 154(b) by 0 days.

(21) Appl. No.: 12/533,372

(22) Filed: Jul. 31, 2009

Related U.S. Application Data

(60) Provisional application No. 61/169,500, filed on Apr. 15, 2009.

(51) Int. Cl.
*A61Q 5/10* (2006.01)
(52) U.S. Cl. .................. 8/405; 8/435; 8/552; 8/554
(58) Field of Classification Search .............. 8/405, 8/435, 552, 554
See application file for complete search history.

(56) References Cited

U.S. PATENT DOCUMENTS

| | | |
|---|---|---|
| 5,357,018 A | 10/1994 | Burkhart et al. |
| 5,807,956 A | 9/1998 | Czech |
| 6,063,369 A | 5/2000 | Pierce et al. |
| 7,204,861 B2 | 4/2007 | Marsh et al. |
| 2003/0064044 A1 | 4/2003 | Chen et al. |
| 2003/0150069 A1 | 8/2003 | Kleen et al. |
| 2004/0133996 A1 * | 7/2004 | Wolff et al. .............. 8/405 |
| 2005/0198747 A1 | 9/2005 | Emmerling et al. |
| 2006/0064823 A1 | 3/2006 | Marsh et al. |
| 2006/0117493 A1 | 6/2006 | Bureiko et al. |
| 2007/0202069 A1 | 8/2007 | Tamareselvy et al. |
| 2008/0233068 A1 | 9/2008 | Forbes et al. |
| 2008/0274071 A1 | 11/2008 | Kaplan |

FOREIGN PATENT DOCUMENTS

| | | |
|---|---|---|
| EP | 1 961 450 A1 | 8/2008 |
| WO | 2006051246 A1 | 5/2006 |
| WO | 2007063024 A2 | 6/2007 |

OTHER PUBLICATIONS

STIC Search Report dated Jun. 8, 2010.*
Momentive Performance Materials, "Silsoft* A-843 organosilicon copolymer" pp. 1-8; www.momentive.com.
Momentive Performance Materials, "Silsoft Tone* color retaining conditioning agent", pp. 1-8; www.momentive.com.
"euxyl PE9010"; www. schuelke_mayr.com/download/pdf/cint_lint_euxyl_PE_9010_prod.pdf.
Product Information "Dow Corning CE 8401 Emulsion"; pp. 1-6; www2.dowcorning.com/DataFiles/09007c88020f7d5.pdf.
Croda, "OptaSenseTM Liquid Dispersion Polymers", pp. 1-22; www.croda.com (Nov. 2006).
Product Information "Versene 100 XL Chelating Agent", pp. 1-2; www.dowcorning.com.

* cited by examiner

*Primary Examiner*—Eisa B Elhilo
(74) *Attorney, Agent, or Firm*—Brooks Kushman P.C.

(57) ABSTRACT

The present invention relates to a hair care component and method of manufacture for use in a hair coloring system. In one embodiment of the invention, a hair care component for use in a hair coloring system includes a mixture resulting from blending an aqueous solution, an emulsion, and a cationic water-in-oil liquid dispersion of an alkylene, olefinically unsaturated (alkyl)amide. The emulsion includes a polysiloxane (A)-polyoxyalkylene (B) block copolymer of an $(A-B)_n$-type. The copolymer includes an aminofunctional silicone. The liquid dispersion inverts from the water-in-oil phase to an oil-in-water phase when mixed with the aqueous solution.

20 Claims, No Drawings

US 7,833,289 B1

HAIR CARE COMPONENT AND METHOD OF MANUFACTURE FOR USE IN A HAIR COLORING SYSTEM

CROSS-REFERENCE TO RELATED APPLICATIONS

This application claims the benefit of U.S. provisional application Ser. No. 61/169,500 filed Apr. 15, 2009.

BACKGROUND OF THE INVENTION

1. Field of the Invention

The present invention relates to a hair care component and method of manufacture for use in a hair coloring system.

2. Background Art

Some people apply a colorant to their hair. During the application, many hair coloring systems use a strongly alkaline solution to open the cuticle of the hair. With the cuticle open, the colorant may penetrate further into the interior of the hair. The cuticle of the hair is then closed by rinsing with relatively neutral pH water or rinsing solution.

But, the colorant typically is washed out by repeated shampooing within a relatively short period of time. Even while the colorant is present, repeated washing causes incremental loss of the colorant that reduces the color intensity and the coverage of gray hair.

Some polymers have been used to slow the incremental loss of the colorant while retaining the color intensity and gray coverage. The use of a strongly alkaline solution in the hair coloring system, such as those having a pH greater than 9, often is detrimental to many polymers' functional effectiveness. The alkalinity may disrupt the polymers' tertiary structure and/or hydrogen bonding. The disruption typically makes substantial changes to the polymers' properties, such as viscosity. As a consequence, the polymers are included in a second solution that may be blended with the alkaline-solution colorant once the colorant has been applied to the hair. Such blending provides opportunities for inaccurate or inhomogeneous mixing. Incorrect mixing may result in an unacceptable hair coloring experience.

What is needed is a hair care component, which can assist in increasing the colorant penetration into the interior of the hair and in extending the time period between colorings of the hair. The hair care component further needs to be compatible with typical hair coloring systems that use strongly alkaline solutions and be suitable for blending with the hair coloring system prior to application to the hair.

SUMMARY OF THE INVENTION

The present invention relates to a hair care component and method of manufacture for use in a hair coloring system. In one embodiment of the invention, a hair care component for use in a hair coloring system includes a mixture resulting from blending an aqueous solution, an emulsion, and a cationic water-in-oil liquid dispersion of an alkylene, olefinically unsaturated (alkyl)amide. The emulsion includes a polysiloxane (A)-polyoxyalkylene (B) block copolymer of an $(A-B)_n$-type. The copolymer includes an aminofunctional silicone. The liquid dispersion inverts from the water-in-oil phase to an oil-in-water phase when mixed with the aqueous solution.

In another embodiment of the invention, the hair care component includes a mixture resulting from blending an alkaline aqueous solution, a hair care potentiator and a cationic sealing emulsion. The potentiator includes an aminofunctional silicone polyether block copolymer emulsion. The cationic sealing emulsion has a viscosity in the alkaline solution ranging from 500 centipoise to 4500 centipoise.

In another embodiment of the invention, the method of manufacture of the hair care component includes blending an emulsion comprising a polysiloxane (A)-polyoxyalkylene (B) block copolymer of an $(A-B)_n$-type and a cationic water-in-oil dispersion having alkylene, olefinically unsaturated (alkyl)amide to form a first mixture. The copolymer includes an aminofunctional silicone. The method further comprises blending the first mixture with water to form a second mixture.

DETAILED DESCRIPTION OF THE PREFERRED EMBODIMENT(S)

Reference will now be made in detail to presently preferred compositions, embodiments and methods of the present invention, which constitute the best modes of practicing the invention presently known to the inventors. But, it should be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the operating examples, or where otherwise expressly indicated, all numbers in this description indicating material amounts, reaction conditions, or uses are to be understood as modified by the word "about" in describing the invention's broadest scope. Practice within the numerical limits stated is generally preferred. Also, unless expressly stated to the contrary:

percent and ratio values are by weight;

the term "polymer" includes "oligomer," "copolymer," "dimer," "terpolymer," "tetramer" and the like;

a material group or class described as suitable or preferred for a given purpose in connection with the invention implies any two or more of these materials may be mixed and be equally suitable or preferred;

constituents described in chemical terms refer to the constituents at the time of addition to any combination specified in the description, and does not preclude chemical interactions among mixture constituents once mixed;

an acronym's first definition or other abbreviation applies to all subsequent uses here of the same abbreviation and mutatis mutandis to normal grammatical variations of the initially defined abbreviation; and unless expressly stated to the contrary, measurement of a property is determined by the same technique as previously or later referenced for the same property.

In at least one embodiment, the present invention provides hair care component, such as a hair color serum, for use in a hair coloring system. The hair color serum is a convenient mechanism for isolating compatible ingredients for later blending with another solution, such as a colorant solution, with which the hair care component's ingredients may or may not be compatible.

In at least one embodiment of the present invention, the hair color serum includes a potentiator, which enhances the effect of other ingredients in the serum, and a sealant. In another embodiment, the hair color serum may also include one or more of a thickener; a film former; and a chelator. Moreover, the color serum may further include one or more of a cationic organic, such as a cationic hempseed ingredient; a bioactive enzyme; and a product to mask odors such as ammonia found in hair coloring solutions.

The potentiator for enhancing the binding of a hair colorant to the hair may include a silicone compound, such as a polysiloxane. A non-limiting example of the polysiloxane is an aminofunctional silicone, such as an amodialkylicone like an amodimethicone. The aminofunctional silicone may be further enhanced when it is formulated as a copolymer with a polyoxyalkylene, especially when the amodimethicone is formulated as a block copolymer with the polyoxyalkylene.

A non-limiting example of the polysiloxane (A) and polyoxyalkylene (B) block copolymer includes a copolymer with an $(A-B)_n$-type structure, where n exceeds 3. In another embodiment, the copolymer may have 3-10 blocks, i.e. n ranges from 3 to 10. It should be understood that other structures of the AB-type copolymers, including random copolymers, may be used without exceeding the scope of this invention.

A non-limiting example of the polyoxyalkylene may include a polyether.

The block copolymer can be further enhanced when it is formulated as an emulsion. In one embodiment, the emulsion is a water-in-oil emulsion, an example of which is supplied as Dow Corning® CE 8401 emulsion provided by Dow Corning Corporation (Midland, Mich.). In another embodiment, the emulsion is an inverse emulsion, such as an oil-in-water emulsion.

In at least one embodiment of the invention, the polysiloxane-polyoxyalkylene block copolymer emulsion comprises a range from 0.5 wt. % to 10 wt. % of the weight of the hair care component. In another embodiment, the polysiloxane-polyoxyalkylene block copolymer comprises a range from 1.5 wt. % to 7 wt. % of weight of the hair care component. In yet another embodiment, the polysiloxane-polyoxyalkylene block copolymer comprises a range from 3 wt. % to 5 wt. % of the weight of the hair care component. It should be understood that the weight % composition is expressed on an "as-is" basis, which is the weight percentage basis times the percent solids basis. In the above embodiments, since in some embodiments the copolymer is substantially 100% solids, the emulsion may comprise either the weight ranges "as-is" or as percent solids without exceeding the scope of the invention.

A non-limiting example of the sealant may include a cationic water-in-oil liquid dispersion having a polymer, such as an alkylene, olefinically unsaturated (alkyl)amide. A non-limiting example of the alkylene, olefinically unsaturated (alkyl)amide includes a cationic alkylene bis(meth)acrylamide, such as a quaternary ethylene bis(meth)acrylamide.

In at least one embodiment of the invention, the cationic water-in-oil liquid dispersion includes a rheology control agent, such as an inversion agent in an oil phase of the emulsion. The liquid dispersion having the inversion agent prevents thickening when at relatively high concentration. Upon dilution, the cationic water-in-oil liquid dispersion emulsion inverts to form an oil-in-water emulsion to induce thickening of the water phase. A non-limiting example of the rheology control agent may be a polyoxypropylene, polyoxyethylene ether of tridecyl alcohol. A non-limiting example of the oil phase may include hydrogenated polydecene.

In at least one embodiment of the invention, the sealant comprises a weight ranging from 0.10 wt. % to 10 wt. % of the weight of the hair care component. In another embodiment, the sealant comprises a weight ranging from 0.5 wt. % to 7 wt. % of the weight of the hair care component. In yet another embodiment, the sealant comprises a weight ranging from 1 wt. % to 3 wt. % of the weight of the hair care component.

In at least one embodiment, the percentage solids is 92%. Therefore, in at least one embodiment, the sealant comprises a weight ranging from 0.09-9.2 wt. % on a percent solids basis of the weight of the hair care component. In another embodiment, the sealant comprises a weight ranging from 0.45 wt. % to 6.3 wt. % on a percent solids basis of the weight of the hair care component. In yet another embodiment, the sealant comprises a weight ranging from 0.92 wt. % to 2.7 wt. % on a percent solids basis of the weight of the hair care component.

In at least one embodiment, the active component comprises 55 wt. % of the sealant. In at least one embodiment, the active component of the sealant comprises a weight ranging from 0.05 wt. % on an active component percent solids basis of the weight of the hair care component to 5.1 wt. % on the same basis. In another embodiment, the active component of the sealant comprises a weight ranging from 0.25 wt. % on an active component percent solids basis of the weight of the hair care component to 3.6 wt. % on the same basis. In yet another embodiment, the active component of the sealant comprises a weight ranging from 0.5 wt. % on an active component percent solids basis of the weight of the hair care component to 1.5 wt. % on the same basis.

Non-limiting examples of the sealant are supplied as Optasense® RMC70 provided by Croda Inc. (Edison, N.J.), Salcare® provided by Ciba-Geigy (Tarrytown, N.Y.), or Rheocare® provided by Cognis IP Management GmbH (Düsseldorf, Germany).

The hair care component may be used in a hair coloring system that has a colorant solution including a colorant and an alkalinity reagent, such as an ammoniacal or a peroxide component. In at least one embodiment, the hair color serum has a pH ranging from 4.5 to 5.5 at 20° C. The colorant solution and/or the hair coloring system generally have a pH exceeding 9. In another embodiment, the colorant solution and/or the hair colorant system have a pH of 9 or more. In another embodiment, the colorant solution and/or the hair coloring system have a pH ranging from 9.1 to 10.5. It is understood that the pH of the hair coloring system may be adjusted to an alkaline pH through addition of alkalinity reagents, such as ammonia or peroxide, to any of the solutions in the hair care component, like the colorant solution, the aqueous solution, or the mixture of the hair care component with the colorant solution without exceeding the scope of the invention.

In at least one embodiment of the invention, the sealant has a viscosity ranging from 300 centipoise to 2500 centipoise in the alkaline solution of the hair color system. In another embodiment, the sealant has a viscosity ranging from 700 centipoise to 2000 centipoise in the alkaline solution of the hair color system. In yet another embodiment, the sealant has a viscosity ranging from 750 centipoise to 1500 centipoise in the alkaline solution of the hair color system. The viscosity may be measured using a Brookfield viscometer set at 20 revolutions per minute in a 2 wt. % solution of the sealant, measured according to method ASTM D2857.

Additional embodiments of the hair care component are shown below.

| INGREDIENT | FIRST EMBODIMENT (WT. % PER WT. OF HAIR CARE COMPONENT) | SECOND EMBODIMENT (WT. % PER WT. OF HAIR CARE COMPONENT) | THIRD EMBODIMENT (WT. % PER WT. OF HAIR CARE COMPONENT) | FOURTH EMBODIMENT (WT. % PER WT. OF HAIR CARE COMPONENT) |
|---|---|---|---|---|
| Chelator | 0.00 | 0.00 | 0.01-0.5 | 0.02-0.2 |
| Thickener | 0.00 | 0.00 | 0.1-1 | 0.15-0.5 |
| Liquid dispersion | 10-70 | 0.5-10 | 0.5-8 | 0.75-3 |
| Cationic Hempseedate | 0.00 | 0.00 | 0.25-5 | 0.5-2.5 |
| Film former | 0.00 | 0.00 | 0.25-5 | 0.5-2.5 |
| Active enzymes | 0.00 | 0.00 | 0.01-2 | 0.075-0.25 |
| Potentiator | 30-90 | 0.5-10 | 1-9 | 2-6.5 |
| UV protectant | 0 | 0 | 0.025-1 | 0.05-0.5 |
| Miscellaneous oils and preservatives | 0 | 0 | 0.05-5.1 | 1-2.8 |
| Odor maskant | 0 | 0 | 0.25-2 | 0.5-1.3 |
| Deionized water | 0 | 80-99 | 85-95 | 88-92 |

Further embodiments of the hair care component are shown below.

| INGREDIENT | SOURCE | TYPE | FIRST EMBODIMENT (WT. % PER WT. OF HAIR CARE COMPONENT) | SECOND EMBODIMENT (WT. % PER WT. OF HAIR CARE COMPONENT) | THIRD EMBODIMENT (WT. % PER WT. OF HAIR CARE COMPONENT) |
|---|---|---|---|---|---|
| Deionized water | | Water | 80-99 | 80-95 | 91.3 |
| Versene ® 100 XL | Dow Chemical | Chelator | 0.0-0.5 | 0.01-0.5 | 0.05 |
| Cellosize ® PCG-10 | Amerchol | Thickener | 0.0-1 | 0.1-1 | 0.25 |
| Optasense ® RMC70 | Croda, Inc. | Cationic dispersion | 0.5-10 | 0.5-10 | 1.5 |
| Hempseed Quat Code 09312CT | Arch Personal Care Products LLC | Film former | 0.0-5 | 0.1-4.7 | 0.25 |
| WeGuPrAv Bio-Complex-Certified Organic | Botanica/DKSH | Film Former | 0.0-5 | 0.005-3 | 0.04 |
| Soy-Tein NL-G (Paraben-free) | Kemira, Inc. | Film Former | 0.0-5 | 0.1-4.7 | 0.25 |
| Rice Pro-tein BKG (Paraben-free) | Kemira, Inc. | Film Former | 0.0-5 | 0.1-4.7 | 0.25 |
| Nanozyme BEC-II Plus (Paraben-free) Code 139110 | Arch Personal Care Products LLC | Enzyme Therapy | 0.0-2 | 0.01-2 | 0.02 |
| Photozyme Complete PPS | Active Concepts, LLC | Enzyme Therapy | 0.0-2 | 0.01-2 | 0.02 |
| Dow Corning ® CE 8401 Emulsion | Dow Corning, Inc. | Block Copolymer | 0.5-10 | 1-10 | 4 |
| Incroquat ® UV283 | Croda, Inc. | UV Protectant | 0.01-1 | 0.025-1 | 0.01 |
| Euxyl ® PE9010 | Ross/Schulke & Mayr GmbH | Preservative | 0.0-5 | 0.05-5 | 1 |
| Neolone ® 950 | Rohm & Haas | Preservative | 0.0-5 | 0.01-0.5 | 0.05 |
| Odor mask #FN301329 | Ascent Aromatics | Fragrance | 0.0-2 | 0.25-2 | 0.75 |
| NOP Organic Hemp Oil A99999X | Arbor Organics, LLC/Active Concepts, LLC | Oil | 0.0-1 | 0.1005-0.1 | 0.01 |

The % solids of Versene is 38% and chelators, in general, range from 25% to 50% solids.

The % solids of Cellosize is 100%, and thickeners, in general, are believed to range from 75% to 100% solids.

The % solids of Optasense is 92%, and liquid dispersions, in general, are believed to range from 30% to 95% solids. The active quaternary component is 55% of the solids.

The % solids of Hempseed Quat Code 09312CT is 54%, and film formers, such as plant proteins and extracts, in general, are believed to range from 15% to 60% solids.

The % solids of WeGuPrAv Bio Complex-Certified Organic is 20%.

The % solids of Soy-Tein NL-G is 20%.

The % solids of Rice Pro-Tein BKG is 20%.

The % solids of Nanozyme is 92%, and bioactive enzymes, in general, are believed to range from 2% to 95% solids.

The % solids of Photozyme is 4%.

The % solids of Dow Corning CE8401 emulsion is 20%, and potentiators, in general, range from 30% to 60% solids.

The % solids of NOP Organic Hemp Oil A99999X is 100%.

The % solids of Incroquat UV283 is believed to be 73%, and ultraviolet protectors in general, are believed to range from 60% to 90% solids.

The % solids of Euxyl PE9010 is 100%.

The % solids of Neolone 950 is 11%.

The solids of Odor Mask #FN301329 is 100%.

In at least one embodiment, the hair care system comprises 0.25 oz. of hair color serum in 2-2.5 oz. of the hair color system. For example, the hair system may use 1 oz. of colorant and 1 oz. of a developer to mix with 0.25 oz. of hair color serum.

A coloring process may range from 20 to 40 minutes followed by a rinse with tap water at a pH 5-7 until the water runs clear.

Example 1

A hair care serum is blended according to the following composition:

| INGREDIENT | QUANTITY (wt. % of solution) |
| --- | --- |
| Chelator | 0.05 |
| Thickener | 0.20 |
| Liquid dispersion | 1.5 |
| Cationic Hempseedate | 0.25 |
| Film former | 0.50 |
| Active enzymes | 0.12 |
| Potentiator | 4.0 |
| UV protectant | 0.10 |
| Miscellaneous oils and preservatives | 1.15 |
| Odor maskant | 0.75 |
| Deionized water | 91.38 |

The serum of example 1 may include any of the following ingredients: water, cetyl ethylhexanoate, *cannabis* sativa seed oil, cetyl dimethylamine hydrolyzed hempseedate, *vaccinium vitis-ideaea* fruit extract, *persea gratissima* fruit extract, *wasabia japonica* root extract, *foeniculum vulgare* seed extract, algae extract, saccharomycetes lystae extract, saccharomycetes copper ferment, superoxide dismutase, lactoferrin, *daucus carota* sativa root extract, tocopherol, retinyl palmitate, phospholipids, corn oligosaccharides, copper lysl oxidase, actyl methionine, actyl serine, amino actyl tRNA synthetase, phytosphinosine, *ganoderma lucidum* tyrosinase, *lentinus edodes* tyrosinase, glycine soja seed peroxidase, hydrolyzed rice protein, hydrolyzed soy protein, papain, bromelain, melanin silanetrol, cinnamidopropyltrimonium chloride, polyquaternium-10, polyquaternium-37, glycerin, butylene glycol polysorbate-80, hydrogenated polydecene, trideceth-6, bis-sobutyl polyethylene glycol/polypropylene glycol 20/35 amodimethicone copolymer, hydroxyethylcellulose, tetrasodium ethylenediaminetetraacetic acid, ethylmethylglycerin, phenoxyethanol, methylisothiazolinone, fragrance, alpha-somethyl ionone, benzyl benzoate, citral, hexyl cinnamal, limonene, and/or linalool. In at least some embodiments, excluding water and cetyl ethylhexanoate, some of the ingredients may be present at less than 1 wt. % of the serum.

The pH of the serum, in at least one embodiment of the invention, ranges from 4.5 to 5.5 when measured at 25° C. The serum has a viscosity at the same temperature ranging from 2500 centipoise to 4500 centipoise when measured with an Brookfield RVT viscometer using a number three spindle at 20 revolutions per minute. In at least one embodiment, the serum's specific gravity at 25° C. ranges from 0.98 to 1.03. In at least one embodiment of the invention, the percent solids of the serum ranges from 2 to 7.

The serum is formulated as part of a hair colorant system, in at least one embodiment, by blending a first mixture which includes the potentiator, such as the polysiloxane (A)-polyoxyalkylene (B) block copolymer of the $(A-B)_n$ type having the aminofunctional silicone, and the cationic water-in-oil liquid dispersion, such as the alkylene, olefinically unsaturated (alkyl)amide. That first mixture is then blended with water to form a second mixture. The second mixture, in at least one embodiment, is blended with a hair colorant to form a third mixture, which may include an oxidative dye and/or a nonoxidative dye. The pH of either the water, the second mixture, and/or the third mixture is adjusted to a pH of 9 or greater. It should be understood that the adjustment of the pH may occur either in the serum or in the hair colorant system without exceeding the scope of the invention.

Example 2

The serum of example 1 is comparatively tested in a blind four-week study in which 20 female subjects ranging in age from 18 to 69 years old have one half of their hair dyed with a hair coloring system including the serum, and one half of their hair dyed with the control hair coloring system without the serum. After the application of the hair coloring system, the hair is shampooed, conditioned, and blown dry. A post-application photograph is taken at a predetermined site on each side of the subjects' heads. The photographs are statistically analyzed to determine if there are any significant differences between the sides with regards to gray coverage and color intensity. The statistical analyses are conducted using ImagePro® software.

Other variables such as type of shampoo and conditioner used during the four-week period of the test are controlled. At the conclusion of four weeks, a four-week-after-application photograph is taken and analyzed in the same manner as the post-application photograph. The results are in Tables 1 and 2.

TABLE 1

GRAY COVERAGE

| TIME | GRAY COVERAGE (PERCENTAGE CHANGE FROM POST-APPLICATION) DYE WITH SERUM | GRAY COVERAGE (PERCENTAGE CHANGE FROM POST-APPLICATION) DYE WITHOUT SERUM |
|---|---|---|
| 4-WEEKS AFTER APPLICATION | −5.7% | −31.7% |

In certain embodiments of the invention, the four-week gray coverage of the hair changes from the post-application gray coverage range from 5% more gray coverage to 20% less gray coverage. In other embodiments, the four-week gray coverage of the hair changes from the post-application gray coverage range from 2% more gray coverage to 10% less gray coverage. In yet other embodiments, the four-week gray coverage of the hair changes from the post-application gray coverage range from 1% more gray coverage to 7% less gray coverage.

TABLE 2

COLOR INTENSITY

| TIME | COLOR INTENSITY (PERCENTAGE CHANGE FROM POST-APPLICATION) DYE WITH SERUM | COLOR INTENSITY (PERCENTAGE CHANGE FROM POST-APPLICATION) DYE WITHOUT SERUM |
|---|---|---|
| 4-WEEKS AFTER APPLICATION | 0.4% | −7.4% |

In certain embodiments of the invention, the four-week color intensity of the hair changes from the post-application color intensity range from 2% more intense to 10% less intense. In other embodiments, the four-week color intensity of the hair changes from the post-application color intensity range from 1% more intense to 7% less intense. In yet other embodiments, the four-week color intensity of the hair changes from the post-application intensity range from no change in intensity to 5% less intense.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A hair care component for use in a hair coloring system, the hair care component comprising:
    a mixture resulting from blending:
       an aqueous solution;
       an emulsion comprising a polysiloxane (A)-polyoxyalkylene (B) block copolymer, wherein the copolymer includes an aminofunctional silicone; and
       a cationic water-in-oil liquid dispersion comprising an alkylene, olefinically unsaturated (alkyl)amide, wherein the liquid dispersion inverts from the water-in-oil phase to an oil-in-water phase when mixed with the aqueous solution.

2. The hair care component of claim 1, wherein the polysiloxane comprises an amodialkylicone.

3. The hair care component of claim 1, wherein the polyoxyalkylene comprises a polyether.

4. The hair care component of claim 3, wherein the polysiloxane comprises an amodimethicone.

5. The hair care component of claim 1, wherein the alkylene, olefinically unsaturated (alkyl)amide comprises a quaternary alkylene bis(meth)acrylamide.

6. The hair care component of claim 1, further comprising a cationic hempseed component.

7. The hair care component of claim 6, further comprising at least one of a bioactive enzyme component, a chelator component, a thickener component, and a film former component.

8. The hair care component of claim 1, wherein the emulsion comprises from 0.5 wt % to 10 wt % on a percent solids basis of the weight of the hair care component.

9. The hair care component of claim 1, wherein the emulsion comprises from 3 wt % to 5 wt % on a percent solids basis of the weight of the hair care component.

10. The hair care component of claim 1, wherein the liquid dispersion comprises an active component having a weight ranging from 0.05 wt % to 5.1 wt % on a percent solids basis of the active component of the weight of the hair care component.

11. The hair care component of claim 1, wherein the liquid dispersion comprises an active compound having a weight ranging from 0.45 wt % to 6.3 wt % on a percent solids basis of the active component of the weight of the hair care component.

12. The hair care component of claim 11, wherein the emulsion comprises from 0.5 wt % to 10 wt % of the hair care component.

13. A hair coloring system for use on hair, the hair coloring system comprising:
    a colorant solution including a colorant and either an ammoniacal or a peroxide component, the colorant solution having a pH exceeding 9; and
    the hair care component of claim 1.

14. A hair coloring system of claim 13, wherein the hair coloring system, when applied to the hair, imparts a first color intensity to the hair, the color intensity of the hair being a second color intensity at four weeks after the application of the hair color system to the hair, the second color intensity ranging from 5% less than the first color intensity to 2% greater than the first color intensity when measured using color intensity image analysis.

15. A hair coloring system of claim 13, wherein the hair coloring system, when applied to the hair, imparts a first gray coverage to the hair, the gray coverage of the hair being a second gray coverage at four weeks after the application of the hair color system to the hair, the second gray coverage ranging from 20% less than the first gray coverage to 5% greater than the first gray coverage when measured using gray coverage image analysis.

16. A hair care component for use in a hair coloring system, the hair care component comprising:
    a mixture resulting from blending
    an alkaline aqueous solution;
    an aminofunctional silicone polyether block copolymer emulsion hair colorant potentiator; and
    a cationic sealant emulsion which, when in a hair care component, has a viscosity in the alkaline solution ranging from 300 centipoise to 2,500 centipoise.

17. The hair care component of claim 16, further including a hempseedate film former.

18. A hair coloring system for use on hair, the hair coloring system comprising:

a colorant solution including an ammoniacal or a peroxide component and a colorant, the colorant solution having a pH exceeding 9; and the hair care component of claim 16.

19. The method of manufacture of a hair care component for use on hair, the method comprising:

blending an emulsion comprising a polysiloxane (A)-polyoxyalkylene (B) block copolymer, wherein the copolymer includes an aminofunctional silicone, and a cationic water-in-oil liquid dispersion comprising an alkylene, olefinically unsaturated (alkyl)amide to form a first mixture; and blending the first mixture and water to form a second mixture.

20. The method of claim 19, further comprising:

blending the second mixture and a hair colorant to form a third mixture; and adjusting the pH of either the water, the second mixture, or the third mixture to a pH 9 or greater.

* * * * *